United States Patent [19]
Fischer et al.

[11] Patent Number: 5,874,107
[45] Date of Patent: Feb. 23, 1999

[54] SUSTAINED RELEASE TABLET CONTAINING DICLOFENAC-NA AND METHYLHYDROXYPROPYL-CELLULOSE AS A SUSTAINED RELEASE AGENT

[75] Inventors: Wilfried Fischer; Karin Klokkers, both of Holzkirchen, Germany

[73] Assignee: Hexal AG, Holzkirchen, Germany

[21] Appl. No.: 714,063

[22] PCT Filed: Mar. 13, 1995

[86] PCT No.: PCT/EP95/00928

§ 371 Date: Sep. 11, 1996

§ 102(e) Date: Sep. 11, 1996

[87] PCT Pub. No.: WO95/24188

PCT Pub. Date: Sep. 14, 1995

[30] Foreign Application Priority Data

Mar. 11, 1994 [DE] Germany ............... 44 08 326.2

[51] Int. Cl.$^6$ ............... A61K 9/20; A61K 9/22
[52] U.S. Cl. ............ 424/464; 424/465; 424/468; 424/472
[58] Field of Search ............ 424/465, 464, 424/468, 472

[56] References Cited

U.S. PATENT DOCUMENTS 5,236,713  8/1993  Wato et al. ............... 424/443

OTHER PUBLICATIONS

Vyas et al., *Biological Abstracts*, vol. 89, #29721, 1990.

Primary Examiner—Thurman K. Page
Assistant Examiner—Sharon Howard
Attorney, Agent, or Firm—Burgess, Ryan & Wayne

[57] ABSTRACT

The invention relates to a sustained release tablet containing diclofenac-Na as active material and methylhydroxypropylcellulose as sustained release agent.

5 Claims, 4 Drawing Sheets

SUSTAINED RELEASE TABLET CONTAINING DICLOFENAC-NA AND METHYLHYDROXYPROPYL-CELLULOSE AS A SUSTAINED RELEASE AGENT

BACKGROUND OF THE INVENTION

1) Field of the Invention

The object of the present invention is to provide a tablet containing diclofenac-Na which provides sustained release of the active material.

2) Background Art

Tablets containing diclofenac-Na as the active material and hydroxypropylmethylcellulose as carrier and additive are known from WO-A-9 501 781. However, it is desirable to provide sustained release tablets which provide sustained release of the active material, so that an effective plasma concentration of diclofenac-Na is ensured even after a long interval of time (>12 hours).

SUMMARY OF THE INVENTION

This object is met according to the invention by a sustained release tablet containing diclofenac-Na as active material and methylhydroxypropylcellulose as sustained release agent, as well as customary additives, in which the ratio of methylhydroxypropylcellulose to diclofenac-Na amounts to $\geq 0.3$.

It has been shown in in vitro experiments that tablets with a total content of 150.0 mg diclofenac-Na and 35.0 mg methylhydroxypropylcellulose per tablet release up to 100% sustained over approximately eight hours (Method: USP XXII, Paddle apparatus). However, it has unexpectedly been found that this sustained release effect is not present in vivo; rather a delay of only approximately 1 hour can be attained. Accordingly it was not to be expected that an alteration in the ratio of methylhydroxypropylcellulose to diclofenac-Na would allow a satisfactory sustained release in vivo to be obtained. Thus for example, with a two-layer sustained release tablet according to the invention with a total content of diclofenac-Na of 150.0 mg diclofenac-Na per tablet and a ratio of methylhydroxypropylcellulose to diclofenac-Na in the sustained release part of 122.5:125.0 and a ratio of methylhydroxypropylcellulose to diclofenac-Na in the initial part of 0:25 allowed a sustained release of approximately 15 hours to be attained in vivo.

DESCRIPTION OF THE PREFERRED EMBODIMENTS

According to a particular embodiment a sustained release tablet according to the invention comprises (a) a tablet portion containing diclofenac-Na and methylhydroxypropylcellulose with a ratio of methylhydroxypropylcellulose to diclofenac-Na$\geq 0.3$ and (b) an additional tablet portion containing diclofenac-Na and methylhydroxypropylcellulose with a ratio of methylhydroxypropylcellulose to diclofenac-Na<0.3 or without methylhydroxypropylcellulose, as well as customary additives in each, wherein the sustained release tablet is obtainable in that the tablet portions (a) and (b) are made separately from one another and then brought together and the finished sustained release tablet obtained.

The portions (a) and (b) can be pressed together, especially to form a multi-layer tablet.

The invention will now be explained in more detail with reference to examples and figures, in which:

FIG. 1 shows release of diclofenac-Na in vitro from tablets according to example 2, example 3 or comparative example 1;

Figure 1:
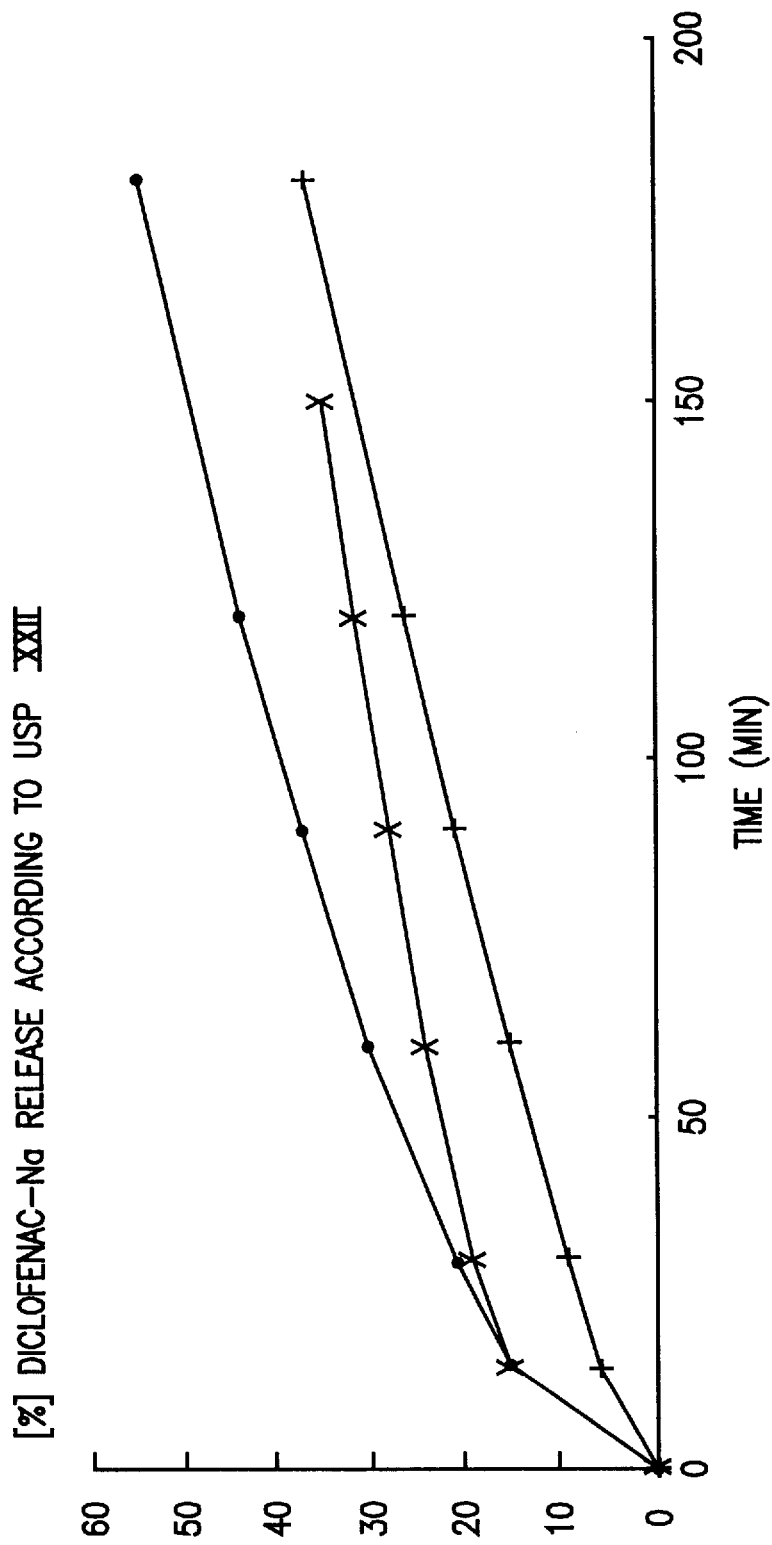

EXAMPLES 1 and 2 sustained release tablets without initial portion

| Example | 1 | 2 |
|---|---|---|
| | [mg per tablet] | |
| 1 diclofenac-sodium | 125.0 | 100.0 |
| 2 lactose.1H$_2$O | 70.4 | 50.0 |
| 3 methylhydroxypropylcellulose | 122.5 | 50.0 |
| 4 colouring | 0.1 | 0.0 |
| 5 water for granulation | | |
| 6 magnesium stearate | 3.5 | 2.0 |
| 7 highly dispersed silicon dioxide | 3.5 | 0.0 |
| | 325.0 | 202.0 |

The colouring (4) was stirred into the water (5). Diclofenac-Na (1), lactose (2) and methylhydroxypropylcellulose (3) were added in a fluidised bed granulator and granulated with the aqueous colouring solution. The resultant granulate as well as magnesium stearate (6) and highly dispersed silicon dioxide (7) were passed through a forced sieve (1.25 mm) and homogenised in a container mixer. The resultant mixture was pressed into tablets on a rotating table tablet machine.

The release of diclofenac-Na according to USP XXII of a tablet according to example 2 can be seen from FIG. 1.

EXAMPLE 3

Tablet with initial and sustained release portions (two-layer tablet).

| | [mg per tablet] |
|---|---|
| 1–7 as example 1 | 325.0 |
| 8 diclofenac-sodium | 25.0 |
| 9 lactose. 1H$_2$O | 15.0 |
| 10 CaHPO$_4$. 2H$_2$O | 20.0 |
| 11 microcrsyt. cellulose | 24.5 |
| 12 maize starch | 10.0 |
| 13 Na-carboxymethyl starch | 4.0 |
| 14 magnesium stearate | 1.0 |
| 15 highly dispersed silicon dioxide | 0.5 |
| | 425.0 |

Example 1 was repeated. The above components (8) to (15) were passed though a forced sieve (0.8 mm) and homogenised in a container mixer. The resulting mass was pressed on to the sustained release portion according to example 1 as an initial portion or second layer, to form a two-layer tablet.

The release of diclofenac-Na according to USP XXII can be seen in FIG. 1.

Comparative Example 1

Two-layer tablet.

|   | [mg per tablet] |
|---|---|
| 1 diclofenac-sodium | 125.0 |
| 2 lactose. 1H$_2$O | 87.5 |
| 3 methylhydroxypropylcellulose | 35.0 |
| 4 colouring | 0.0 |
| 5 water for granulation | |
| 6 magnesium stearate | 2.5 |
| 7 highly dispersed silicon dioxide | 0.0 |
| 8 diclofenac-sodium | 25.0 |
| 9 lactose. 1H$_2$O | 15.0 |
| 10 CaHPO$_4$. 2H$_2$O | 20.0 |
| 11 microcrsyt. cellulose | 24.5 |
| 12 maize starch | 10.0 |
| 13 Na-carboxymethyl starch | 4.0 |
| 14 magnesium stearate | 1.0 |
| 15 highly dispersed silicon dioxide | 0.5 |
|   | 350.0 |

A two-layer tablet was made with the above components as in example 3.

The release of diclofenac-Na according to USP XXII as a function of time can be seen in FIG. 1.

Example of use 1

Figure 2:
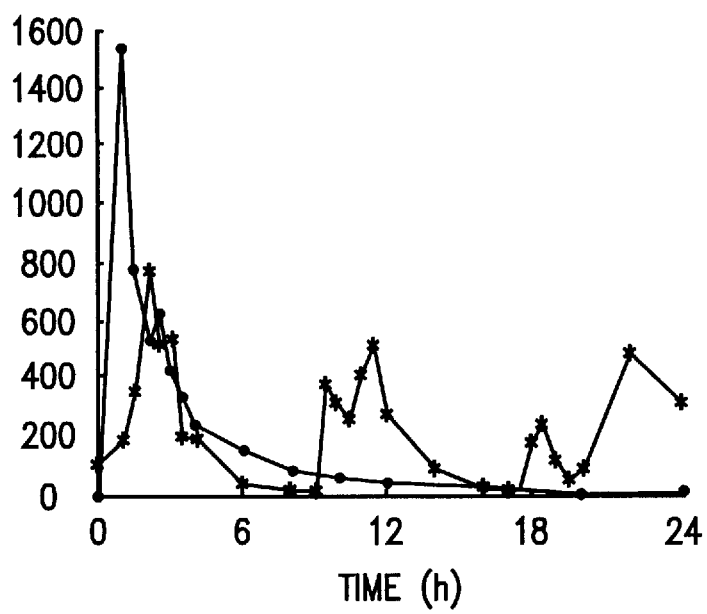
FIG. 2 shows release of diclofenac-Na in vivo of a tablet according to example 1 and a standard tablet in the trade.

The mean diclofenac-Na plasma concentration was determined as follows with eight test subjects. Thus the concentration was followed up for four days beginning with the fourth day after repeated oral administration of one tablet according to example 3 per day (150 mg diclofenac-Na per day), each tablet being given at 8.00 hours. The graph of the plasma concentration is shown in FIG. 2 by white squares.

Example of use 2

Figure 3:
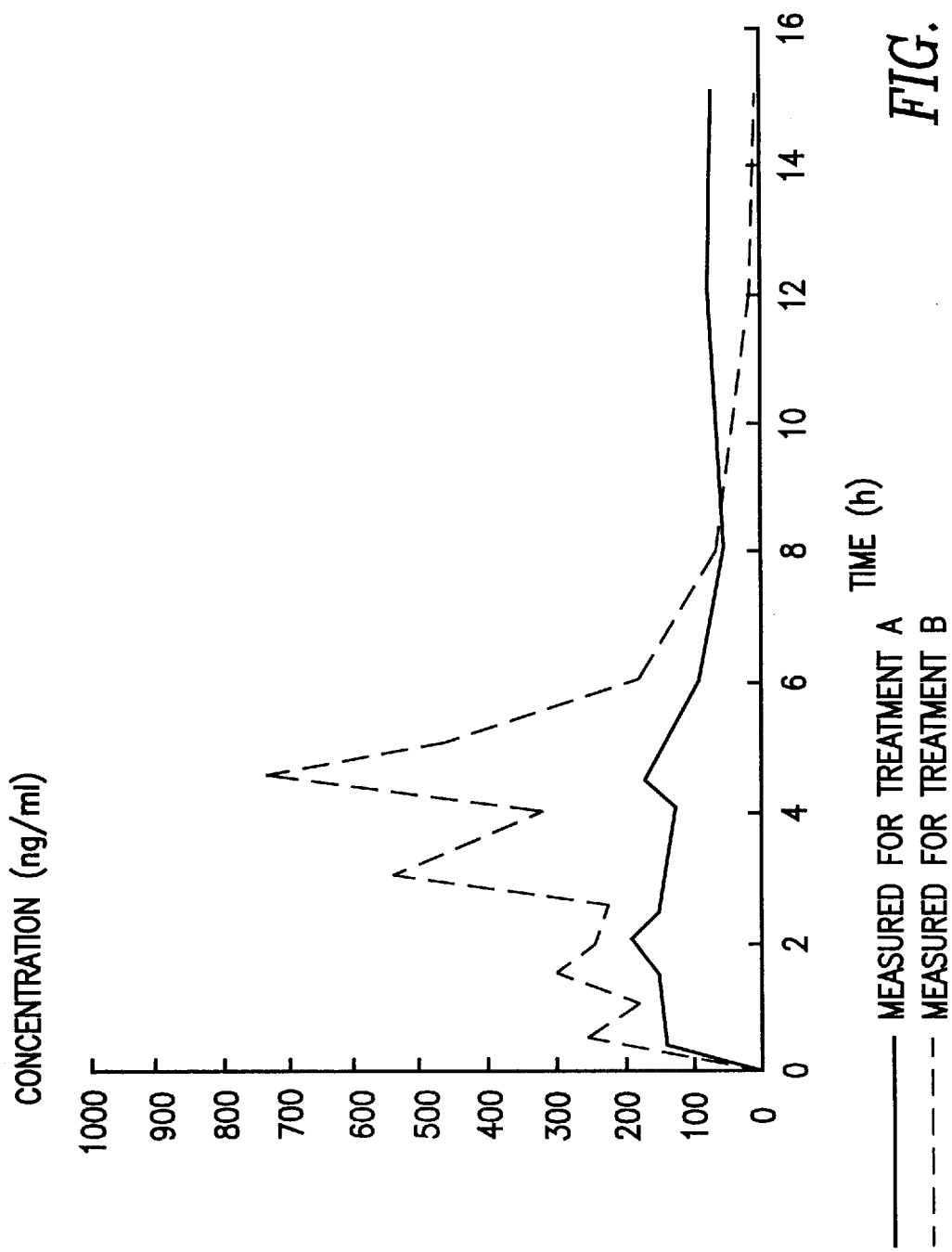
FIG. 3 shows the plasma level of a tablet according to example 2 and standard tablet in the trade.

The mean diclofenac-Na plasma level with a tablet according to example 2 was determined with 12 test subjects, the graph being shown in FIG. 3 by a continuous line.

Comparative example of use 1

Example of use 1 was repeated with the following exceptions. Thus the mean diclofenac-Na concentration was determined beginning with the fourth day after repeated oral administration of diclofenac-Na standard tablets in the trade (50 mg diclofenac-Na per tablet), these being taken at 8.00, 16.00 and 0.00 hours. The graph of the plasma concentration is shown in FIG. 2 by stars.

Both in example of use 1 and in the comparative example of use 1 150 mg diclofenac-Na per day was administered. A comparison of the plasma concentration now shows that even 15 hours after administration of a tablet according to the invention, an appreciable plasma concentration could be observed, while with the comparison tablets the plasma concentration had already fallen to a comparable value after approximately 6 hours.

Comparative example of use 2

In this comparative example of use the plasma level (average over 12 subjects) of a standard diclofenac-Na tablet in the trade (100 mg per tablet) was measured as in example of use 2. The graph of the plasma level is shown in FIG. 3 by a broken line.

Example of use 3

Figure 4:
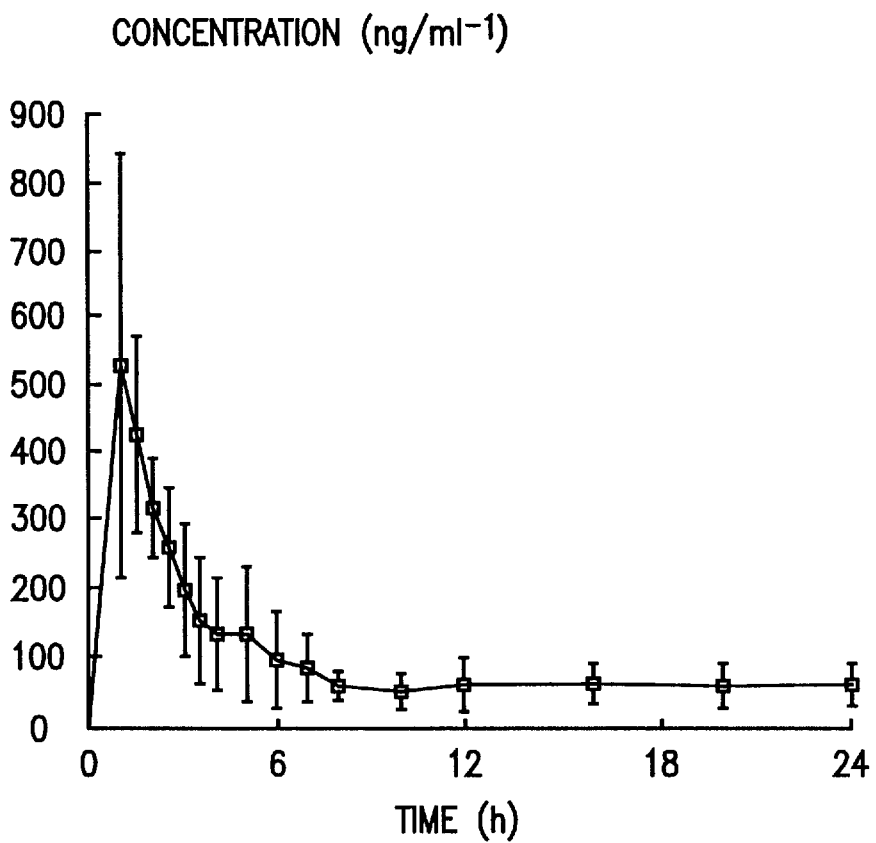
FIG. 4 shows the plasma level (with standard deviation) of a tablet according to example 3 after as single oral administration.

The mean diclofenac-Na plasma level with a tablet according to example 3 (125.0 mg initial portion and 25.0 mg sustained release portion diclofenac-sodium) was followed over 24 hours with 12 test subjects, the graph being reproduced in FIG. 4 by white squares. The standard deviation is represented by vertical bars.

We claim:

1. A sustained release tablet containing diclofenac-Na as active material and methylhydroxypropylcellulose as a sustained release agent, as well as pharmaceutically acceptable additives, having a ratio of methylhydroxypropylcellulose to diclofenac-Na $\geq 0.3$.

2. A sustained release tablet according to claim 1, comprising (a) a tablet portion containing diclofenac-Na and methylhydroxypropylcellulose with a ratio of methylhydroxypropylcellulose to diclofenac-Na$\geq 0.3$ and (b) an additional tablet portion containing diclofenac-Na and methylhydroxypropylcellulose with a ratio of methylhydroxypropylcellulose to diclofenac-Na$\leq 0.3$ or without methylhydroxypropylcellulose as well as pharmaceutically acceptable additives in each and wherein the tablet portions (a) and (b) are made separately from one another and then brought together to form the finished sustained release tablet.

3. A sustained release tablet according to claim 2, wherein the portions (a) and (b) are pressed together.

4. A sustained release tablet according to claim 3, characterized in that the portions (a) and (b) are pressed together into a multi-layer tablet.

5. A method for maintaining an effective plasma concentration of diclofenac-Na for at least 12 hours in a subject which comprises administering to said subject a sustained release tablet according to claim 2.

* * * * *